(12) United States Patent
Wood et al.

(10) Patent No.: US 6,844,452 B2
(45) Date of Patent: Jan. 18, 2005

(54) PROCESS FOR THE CO-PRODUCTION OF ALIPHATIC DIOLS AND CYCLIC ETHERS

(75) Inventors: Michael Anthony Wood, Yarm (GB); Paul Willett, Witton le Wear (GB); Robert Wild, Stockton-on-Tees (GB); Stephen William Colley, Stockton-on-Tees (GB)

(73) Assignee: Davy Process Technology Ltd., London (GB)

( * ) Notice: Subject to any disclaimer, the term of this patent is extended or adjusted under 35 U.S.C. 154(b) by 0 days.

(21) Appl. No.: 10/149,199
(22) PCT Filed: Dec. 12, 2000
(86) PCT No.: PCT/GB00/04758
§ 371 (c)(1), (2), (4) Date: Jun. 10, 2002
(87) PCT Pub. No.: WO01/44148
PCT Pub. Date: Jun. 21, 2001

(65) Prior Publication Data
US 2003/0100777 A1 May 29, 2003

(30) Foreign Application Priority Data
Dec. 13, 1999 (EP) .............................................. 99310003

(51) Int. Cl.$^7$ ............................................. C07D 307/07
(52) U.S. Cl. ........................ 549/475; 549/479; 549/508; 549/509
(58) Field of Search ................................. 549/508, 509, 549/479, 475; 568/864

(56) References Cited

U.S. PATENT DOCUMENTS

| | | | | |
|---|---|---|---|---|
| 4,156,685 A | * | 5/1979 | Tanabe et al. | 549/508 |
| 4,268,447 A | * | 5/1981 | Yoshida et al. | 549/508 |
| 4,795,824 A | * | 1/1989 | Kippax et al. | 560/204 |
| 4,810,807 A | * | 3/1989 | Budge et al. | 549/508 |
| 5,254,758 A | * | 10/1993 | Hiles et al. | 568/881 |
| 5,310,954 A | * | 5/1994 | Hiles et al. | 549/429 |
| 5,395,990 A | | 3/1995 | Scarlett | |

FOREIGN PATENT DOCUMENTS

| | | |
|---|---|---|
| EP | 0 143 634 A2 | 6/1985 |
| WO | WO 86/03189 | 6/1986 |

OTHER PUBLICATIONS

International Search Report for International Application No. PCT/GB 00/04758, mailed Mar. 27, 2001.

* cited by examiner

Primary Examiner—Cecilia J. Tsang
Assistant Examiner—Raymond Covington
(74) Attorney, Agent, or Firm—Senniger Powers

(57) ABSTRACT

A process for the co-production of a diol product (e.g. butane-1,4-diol) and a cyclic ether (e.g. tetrahydrofuran) by hydrogenation of an aliphatic diester or lactone feedstock (e.g. dimethyl or diethyl maleate), which contains a minor amount of acidic material, such as the corresponding monoester. The process utilizes a plurality of hydrogenation zones connected in series, each containing a charge of a granular ester hydrogenation catalyst. The catalyst in the first hydrogenation zone is tolerant of a minor amount of acidic material, while the catalyst in the second hydrogenation zone provides enhanced yields of cyclic ethers compared to the catalyst of the first hydrogenation zone. The catalyst in a third hydrogenation zone exhibits low selectivity towards conversion of the diester to at least one by product (e.g. 2-4'-hydroxybutoxy-tetrahydrofuran). The feedstock is supplied to the first hydrogenation zone as a vaporous stream comprising hydrogen and there is recovered a final product stream from the third hydrogenation zone which is substantially free of the hydrogenatable material and contains the diol, cyclic ether and other by products, the selectivity to the cyclic ether being greater in the final product stream than in the first intermediate product stream.

17 Claims, 2 Drawing Sheets

PROCESS FOR THE CO-PRODUCTION OF ALIPHATIC DIOLS AND CYCLIC ETHERS

Figure 1:
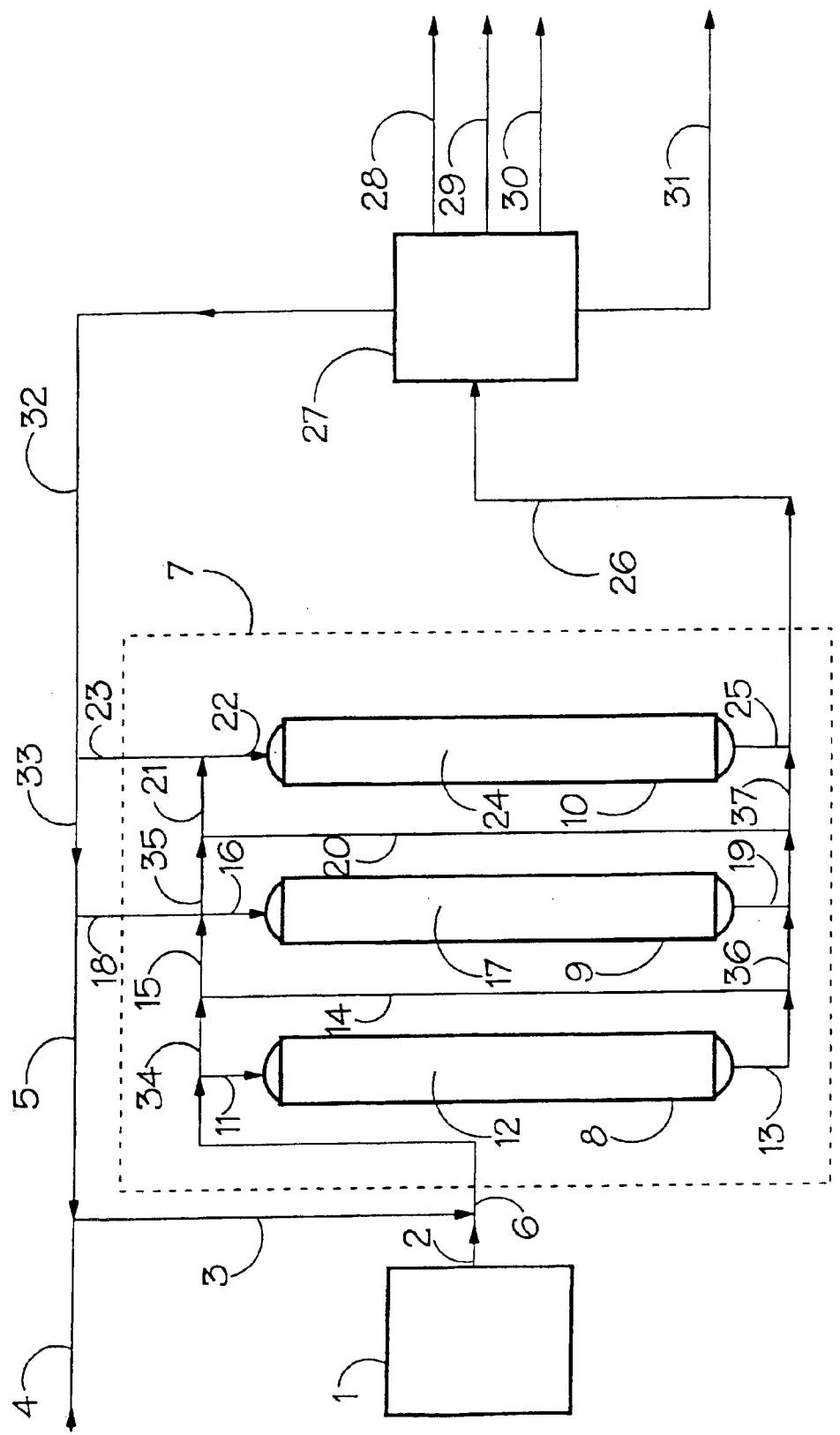

This invention relates to the co-production of aliphatic diols, and cyclic ethers by hydrogenation of a hydrogenatable material which is a dialkyl ester of a dicarboxylic acid, a lactone of an aliphatic hydroxycarboxylic acid, a mixture thereof or a mixture of one or both thereof with a minor amount of a corresponding monoalkyl ester of an aliphatic dicarboxylic acid. In particular it relates to the co-production of $C_4$ to $C_{12}$ aliphatic diols and corresponding cyclic ethers by hydrogenation of di-($C_1$ to $C_4$ alkyl) esters of $C_4$ to $C_{12}$ aliphatic dicarboxylic acids.

It is known to produce aliphatic diols by hydrogenation of dialkyl esters of aliphatic dicarboxylic acids, lactones, and mixtures thereof with a minor amount, typically no more than about 2 wt/wt %, of a monoester of the aliphatic dicarboxylic acid. Thus commercial plants have been built which produce mixtures of butane-1,4-diol, tetrahydrofuran and γ-butyrolactone by hydrogenation of a dialkyl ester of maleic acid, such as dimethyl maleate or diethyl maleate. Dimethyl succinate or diethyl succinate have also been suggested as suitable starting materials for hydrogenation to produce butane-1,4-diol, tetrahydrofuran and γ-butyrolactone.

For further information regarding the operation of such plants reference may be made, for example, to U.S. Pat. No. 4,584,419, U.S. Pat. No. 4,751,334, WO-A-86/03189, WO-A-88/00937, U.S. Pat. No. 4,767,869, U.S. Pat. No. 4,945,173, U.S. Pat. No. 4,919,765, U.S. Pat. No. 5,254,758, U.S. Pat. No. 5,310,954, and WO-A-91/01960, the disclosure of each of which is herein incorporated by reference.

Although many plant operators desire to maximise the yield of butane-1,4-diol and to minimise the yield of the major co-products, γ-butyrolactone and tetrahydrofuran, these major co-products are themselves also valuable commodity chemicals. In some cases the plant operator will, in particular, have a ready market for tetrahydrofuran and will desire to enhance the yield of this co-product rather than to suppress it.

One commercially practised method for the production of the dialkyl maleates which are used as feedstock in such hydrogenation processes involves reaction of maleic anhydride with an alkanol, such as methanol or ethanol, to form first the corresponding monoalkyl maleate and then to convert the monoalkyl maleate to the corresponding dialkyl maleate. The reaction between maleic anhydride and the $C_1$ to $C_4$ alkanol to form the corresponding mono-($C_1$ to $C_4$ alkyl) maleate can be auto-catalysed and proceeds according to the reaction:

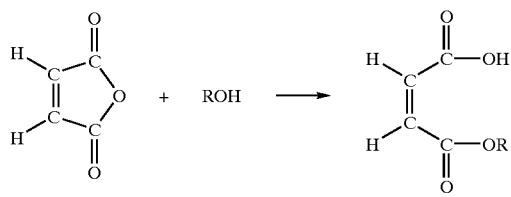

where R is a $C_1$ to $C_4$ alkyl radical. The mono-($C_1$ to $C_4$ alkyl) maleate then reacts with further $C_1$ to $C_4$ alkanol in the presence of a catalyst to form the corresponding di-($C_1$ to $C_4$ alkyl) maleate. The reaction concerned is:

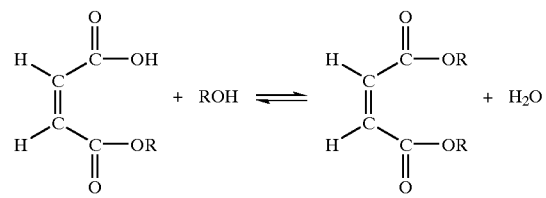

where R is as defined above. The catalytic esterification zone can comprise a plurality of stirred tank reactors, as disclosed in U.S. Pat. No. 4,795,824, but preferably comprises a column reactor of the type disclosed in WO-A-90/08127.

Because the esterification of the monoalkyl maleate is an equilibrium reaction it is difficult to drive the reaction to completion, particularly if the alkanol used for esterification is difficult to dry in an economic manner, such as ethanol. Hence the dialkyl maleate recovered from the esterification reactor often still contains a trace of acidic material, principally the monoalkyl maleate in amounts which typically range from about 0.01 wt/wt % up to about 1.0 wt/wt %. In the process described in WO-A-90/08127, the amount of acidic material in the dialkyl maleate is normally dependent upon the water content of the alkanol vapour stream injected at the bottom of the column reactor. Although the inventors and their co-workers have demonstrated that some heterogeneous ester hydrogenation catalysts are relatively tolerant towards the presence of acidic materials in the dialkyl ester feedstock, such catalysts do not normally give $C_4$ product mixtures with the desired high content of tetrahydrofuran. Moreover other heterogeneous hydrogenation catalysts which yield high proportions of the desirable co-product, tetrahydrofuran, have been found by the inventors and their co-workers to be sensitive to the presence of acidic materials in the feedstock. Examples of such catalysts are described in EP-A-0656336. However, the yield of the undesirable by-product, n-butanol, whose presence can complicate the product recovery procedures, may be somewhat higher than is desirable when such catalysts are used.

Another byproduct whose presence can be give rise to problems is the cyclic acetal, 2-(4'-hydroxybutoxy)-tetrahydrofuran, of the formula:

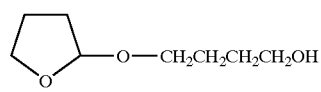

This is presumably formed by reaction of butane-1,4-diol with 4-hydroxybutyraldehyde which is a potential intermediate in the sequence of hydrogenolysis reactions or can be formed by dehydrogenation of butane-1,4-diol itself. The mechanisms for formation of all these products and by-products have not been fully elucidated. However, their production is consistent with the following reaction scheme:

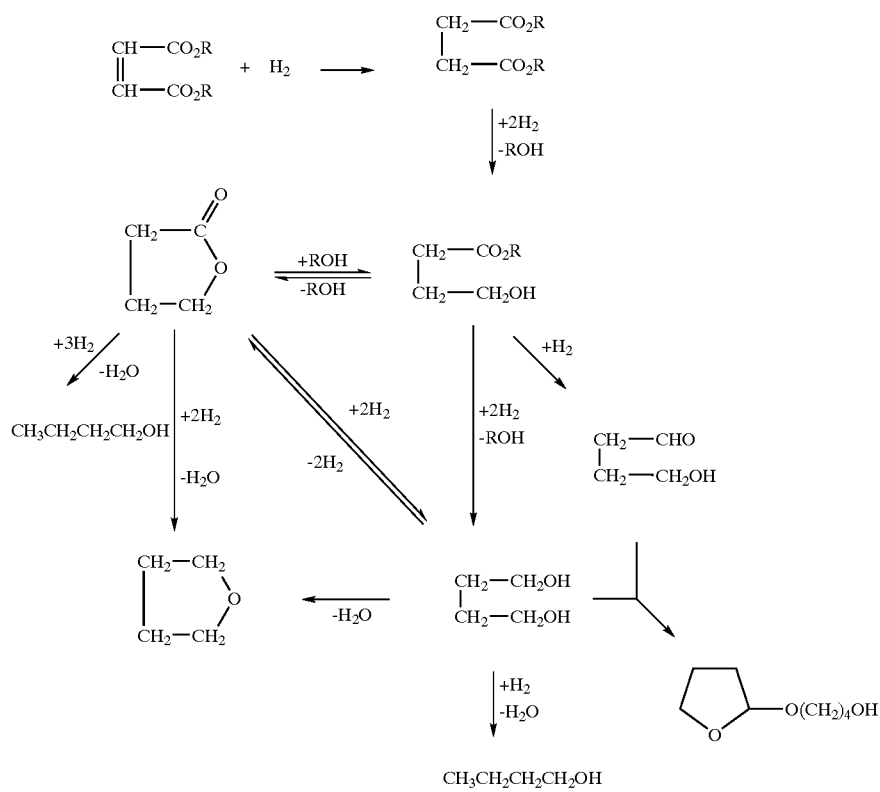

The cyclic acetal by-product, i.e. 2-(4'-hydroxybutoxy)-tetrahydrofuran, is troublesome because its boiling point lies very close to that of butane-1,4-diol and because it forms an azeotrope therewith. For a method for its removal from a butane-1,4-diol stream reference should be made to WO-A-97/36846. It is nevertheless desirable to minimise the formation of this byproduct and of its potential precursors, particularly 4-hydroxybutyraldehyde.

There is accordingly a need for a process for the production in high yield of diols in conjunction with useful co-products including cyclic ethers in which desirably high proportions of useful cyclic ether co-products can be produced. In particular there is a need for the provision of a process for the efficient co-production of butane-1,4-diol and tetrahydrofuran in which a relatively high proportion of the product in molar terms is constituted by tetrahydrofuran. There is also a need to provide such an improved process in which the conversion to the undesirable byproducts n-butanol and the cyclic acetal, 2-(4'-hydroxybutoxy)-tetrahydrofuran, is minimised.

The present invention accordingly seeks to provide an improved process for the co-production of $C_4$ to $C_{12}$ aliphatic diols and the corresponding cyclic ethers thereof by hydrogenation of a corresponding dialkyl ester of a $C_4$ to $C_{12}$ dicarboxylic acid. It further seeks to provide an efficient process for the production of butane-1,4-diol and tetrahydrofuran by hydrogenation of a di-($C_1$ to $C_4$ alkyl) ester of a $C_4$ dicarboxylic acid. In addition it seeks to provide a process for producing relatively high yields of tetrahydrofuran as a co-product, together with γ-butyrolactone, in the production of butane-1,4-diol by hydrogenation of a dialkyl ester of maleic acid or succinic acid, optionally in admixture with the corresponding dialkyl ester of fumaric acid, using as dialkyl ester feedstock a feed ester that contains significant amounts of acidic materials such as the corresponding monoalkyl maleate, fumarate, or succinate. Yet again it seeks to provide an improved process for the co-production of butane-1,4-diol and tetrahydrofuran in which the amounts of the undesirable byproducts n-butanol and the cyclic acetal, 2-(4'-hydroxybutoxy)-tetrahydrofuran, are minimised.

According to the present invention there is provided a process for the co-production of a diol product and a cyclic ether by hydrogenation of a corresponding hydrogenatable material selected from monoesters of dicarboxylic acids, diesters of dicarboxylic acids, lactones, and mixtures of two or more thereof, which comprises:

providing a plurality of hydrogenation zones including first, second and third hydrogenation zones connected in series, the hydrogenation zones each containing a charge of a granular ester hydrogenation catalyst, the first hydrogenation zone containing a bed of a catalyst which is tolerant of the presence of a minor amount of acidic material, the second hydrogenation zone containing a bed of a catalyst which provides enhanced selectivity to the cyclic ether compared to the catalyst of the first hydrogenation zone, and the third hydrogenation zone containing a bed of a catalyst which exhibits a reduced selectivity to at least one byproduct compared with the catalyst of the second hydrogenation zone;

maintaining each of the plurality of hydrogenation zones under temperature and pressure conditions effective for the hydrogenation of the hydrogenatable material to a diol product;

supplying to the first hydrogenation zone a vaporous stream comprising hydrogen and the hydrogenatable material, the hydrogenatable material containing a minor amount of acidic material;

recovering from the first hydrogenation zone a first intermediate product stream containing unreacted hydrogenatable material, diol, lactone, cyclic ether and one or more byproducts;

supplying material of the first intermediate product stream to the second hydrogenation zone;

recovering from the second hydrogenation zone a second intermediate product stream comprising unreacted hydrogenatable material, diol, lactone, cyclic ether, and one or more byproducts, the selectivity to the cyclic ether being higher in the second intermediate product stream than in the first intermediate product stream;

supplying material of the second intermediate product stream to the third hydrogenation zone; and recovering from the third hydrogenation zone a final product stream which is substantially free of the hydrogenatable material and which contains the diol, lactone, cyclic ether and other byproduct, the selectivity to the cyclic ether being greater in the final product stream than in the first intermediate product stream.

Preferably the selectivity to the at least one byproduct is less in the final product stream than in the second intermediate product stream.

In a particularly preferred process the hydrogenation catalyst of the first hydrogenation zone is selected from a noble metal hydrogenation catalyst and a copper-containing hydrogenation catalyst. Hence the catalyst of the first hydrogenation zone can be a palladium catalyst, a reduced copper chromite catalyst or a reduced promoted copper chromite catalyst.

It is also preferred that the catalyst in at least one of the second and third hydrogenation zones is a copper-containing catalyst. In one preferred process the catalyst of the first, second and third hydrogenation zones is a copper-containing catalyst.

As copper-containing catalysts there can be mentioned reduced copper oxide/zinc oxide hydrogenation catalysts, reduced manganese promoted copper catalysts, reduced copper chromite catalysts, and reduced promoted copper chromite catalysts.

The catalyst of at least one of the second and third hydrogenation zones can be, for example, a reduced manganese promoted copper catalyst.

When the hydrogenation catalyst in each of the plurality of hydrogenation zones is a copper-containing catalyst, the active catalytic species in such a catalyst may be at least partially supported on a supporting material selected from chromia, zinc oxide, alumina, silica, silica-alumina, silicon carbide, zirconia, titania, carbon, or a mixture of two or more thereof, for example, a mixture of chromia and carbon.

The hydrogenation catalyst used in the first hydrogenation zone is selected so as to be tolerant of minor amount of acidic materials, more particularly acidic organic materials, such as a monoester of a dicarboxylic acid, which may be present in the hydrogenatable material in amounts up to about 5 wt/wt %, typically no more than about 2 wt/wt %, and more usually in the range of from about 0.005 wt/wt % up to about 1 wt/wt %. Examples of such acidic organic materials, which may be present when the hydrogenatable material comprises a dialkyl maleate or succinate, include the corresponding monoalkyl maleate, fumarate or succinate.

Under normal operating conditions it will be preferred to operate with a hydrogenatable material that has as low an acid content as practicable, e.g. with an acidic material content of from about 0.01 to about 0.25 wt/wt %. However, it may happen that, as a result, for example, of the operating conditions in the production plant for the hydrogenatable material being perturbed, the level of the acidic material in the hydrogenatable material may temporarily rise to about 1.0 wt/wt % or higher.

In a preferred process according to the invention the catalyst of the first hydrogenation zone is a reduced copper chromite catalyst or a reduced promoted copper chromite catalyst. A suitable reduced copper chromite catalyst has, in the unreduced form, a total surface area of at least about 20 $m^2/g$, a pore size distribution such that less than 50% of the pore volume is provided by pores in the size range less than about 40 nm, and a surface area distribution such that less than 50% of the total surface area is provided by pores in the size range of from about 7 nm to about 40 nm. A copper chromite catalyst of this type is, for example, the catalyst sold as PG85/1 catalyst by Kvaerner Process Technology Limited of The Technology Centre, Princeton Drive, Thornaby, Stockton-on-Tees, TS17 6PY, England.

It is also preferred that the catalyst of the second hydrogenation zone should be a reduced manganese promoted copper catalyst. Such a reduced manganese promoted copper catalyst may have, in the unreduced form, a total surface area of at least about 15 $m^2/g$, a pore size distribution such that more than 50% of the pore volume is provided by pores in the size range less than about 40 nm, and a surface area distribution such that more than 50% of the total surface area is provided by pores of less than about 7 nm. A catalyst of this type, which exhibits a markedly higher selectivity towards production of tetrahydrofuran under typical operating conditions when dimethyl or diethyl maleate is subjected to hydrogenation than PG85/1 reduced copper chromite catalyst, is sold as DRD92/89B catalyst by Kvaerner Process Technology Limited.

The third hydrogenation zone contains a bed of a hydrogenation catalyst which exhibits a reduced selectivity to at least one byproduct under typical operating conditions when dimethyl or diethyl maleate is subjected to hydrogenation compared with the corresponding activity exhibited by the catalyst of the second hydrogenation zone. A suitable catalyst is a reduced manganese promoted copper catalyst which has, in the unreduced form, a total surface area of at least about 15 $m^2/g$, a pore size distribution such that more than 50% of the pore volume is provided by pores in the size range less than about 40 nm, and a surface area distribution such that more than 50% of the total surface area is provided by pores in the size range of from about 7 nm to about 40 nm. A catalyst suitable for use in the third hydrogenation zone in such a process is DRD92/89A catalyst which is also commercially available from Kvaerner Process Technology Limited. This catalyst exhibits a lower selectivity towards the cyclic acetal, 2-(4'-hydroxybutoxy)-tetrahydrofuran than DRD92/89B catalyst, when dimethyl maleate or diethyl maleate is subjected to hydrogenation under typical commercial operating conditions.

In a particularly preferred process the first hydrogenation zone contains a charge of a reduced copper chromite catalyst, while the second hydrogenation zone contains a charge of a reduced manganese promoted copper catalyst which has, in the unreduced form, a total surface area of at least about 15 $m^2/g$, a pore size distribution such that more than 50% of the pore volume is provided by pores in the size range less than about 40 nm, and a surface area distribution such that more than 50% of the total surface area is provided by pores of less than about 7 nm, and the third hydrogenation zone contains a charge of a reduced manganese promoted copper catalyst which has, in the unreduced form, a total surface area of at least about 15 $m^2/g$, a pore size distribution such that more than 50% of the pore volume is provided by pores in the size range less than about 40 nm, and a surface area distribution such that more than 50% of the total surface area is provided by pores in the size range of from about 7 nm to about 40 nm.

The manganese promoted copper catalysts used in the second and third hydrogenation zones preferably have a total surface area of at least about 20 m$^2$/g, and even more preferably at least about 25 m$^2$/g, in the unreduced form. Especially preferred are catalysts of this type which have a total surface area of at least about 35 m$^2$/g, even more preferably at least about 40 m$^2$/g, up to about 55 m$^2$/g or more, in the unreduced form.

For the catalyst of the second hydrogenation zone it is preferred that its surface area distribution in the unreduced form is such that at least about 60% of the total surface area of the catalyst is provided by pores of less than about 7 nm in size. However, for the catalyst of the third hydrogenation zone it is preferred that its surface area distribution in the unreduced form is such that at least about 60%, and even more preferably at least about 70% up to about 85% or more, of the total surface area of the catalyst is provided by pores in the size range of from about 7 nm to about 40 nm.

For the purposes of this invention the values defining the pore sizes are given in nanometers and refer to the nominal radius of each pore. In practice, the pores throughout a catalyst will be of irregular cross section and will not generally be uniform in cross section throughout their length.

The total surface area of a sample of catalyst, which is typically expressed in m$^2$/g, can be measured by an approximation of the well known BET equation as described in ASTM Test Method Designation D 4567-86, entitled "Standard Test Method for Single-Point Determination of Surface Area of Catalysts Using Nitrogen Adsorption by Continuous Flow Method". Preferably, however, the total surface area is measured as described in ASTM Test Method Designation D 3663-92 entitled "Standard Test Method for Surface Area of Catalysts". This describes a method for determining the surface area of a catalyst by measuring the volume of nitrogen gas adsorbed at various low pressure levels by the catalyst sample. Pressure differentials caused by introducing the catalyst surface area to a fixed volume of nitrogen in the test apparatus are measured and used to calculate BET surface area. At least four data points are used.

ASTM Test Method Designation D 4284-92 entitled "Standard Test Method for Determining Pore Volume Distribution of Catalysts by Mercury Intrusion Porosimetry" provides a description of a method by which the pore volume distribution of a catalyst sample can be measured. Typically the pore volume distribution is expressed in mm$^3$/g. In this test the non-wetting liquid mercury is forced into the pores of the catalyst and the volume of the intruded pores is determined by measuring the volume of mercury that is forced into them at various pressures.

From the values obtained for the total surface area of the catalyst and from the pore volume distribution measurements it is then possible to calculate the surface area provided by pores of different pore size ranges.

Typically the hydrogenatable material will contain from about 0.01 to about 0.5 wt/wt % or more, e.g. up to about 5 wt/wt %, but normally no more than about 1.0 wt/wt %, of acidic material.

The charge of catalyst in the first hydrogenation zone is preferably sufficiently large to reduce the content of acidic material to less than about 0.005 wt/wt % in passage of the vaporous mixture therethrough. It will usually be preferred that the volume of catalyst in the first hydrogenation zone constitutes from about 10% to about 70%, more usually from about 20% to about 50%, of the total volume of catalyst in the plurality of hydrogenation zones.

In a typical plant operating a process according to the invention the catalyst of the second hydrogenation zone constitutes from about 10% to about 70% of the total catalyst volume of the plurality of hydrogenation zones. Similarly the catalyst of the third hydrogenation zone is typically in the range of from about 10% to about 70% of the total catalyst volume of the plurality of hydrogenation zones.

The hydrogenatable material is preferably selected from mono-($C_1$ to $C_4$ alkyl) esters of $C_4$ to $C_{12}$ aliphatic dicarboxylic acids, di-($C_1$ to $C_4$ alkyl) esters of $C_4$ to $C_{12}$ aliphatic dicarboxylic acids, lactones of $C_4$ to $C_{12}$ aliphatic hydroxycarboxylic acids, and mixtures of two or more thereof. For example, the hydrogenatable material can be selected from mono-($C_1$ to $C_4$ alkyl) esters of $C_4$ aliphatic dicarboxylic acids, di-($C_1$ to $C_4$ alkyl) esters of $C_4$ aliphatic dicarboxylic acids, γ-butyrolactone, and mixtures of two or more thereof. A particularly preferred hydrogenatable material can be selected from monomethyl maleate, monomethyl fumarate, monomethyl succinate, dimethyl maleate, dimethyl fumarate, dimethyl succinate, γ-butyrolactone, and mixtures of two or more thereof. Alternatively the hydrogenatable material can be selected from monoethyl maleate, monoethyl fumarate, monoethyl succinate, diethyl maleate, diethyl fumarate, diethyl succinate, γ-butyrolactone, and mixtures of two or more thereof.

It is further preferred that the feed stream to each of the hydrogenation zones is a vaporous feed stream and that the final product stream is recovered in vaporous form. Alternatively the final product can be recovered as a mixture of liquid and vapour at a temperature below the dew point of the stream. In this case the feed stream to at least one hydrogenation zone downstream from the first hydrogenation zone can also be a mixture of vapour and liquid at a temperature below the dew point of the mixture. However, the feed stream to the first hydrogenation zone should in all cases be a vaporous stream.

It will normally be preferred that, in the vaporous feed stream to the first hydrogenation zone, the hydrogen-containing gas:hydrogenatable material molar ratio shall be in the range of from about 50:1 to about 1000:1.

Typically the feed temperature to the first hydrogenation zone is from about 100° C. to about 300° C., more preferably from about 150° C. to about 250° C., while the feed pressure to the first hydrogenation zone is from about 50 psia (about 344.74 kPa) to about 2000 psia (about 13789.52 kPa), for example, from about 450 psia (about 3102.64 kPa) to about 1000 psia (about 6894.76 kPa). The hydrogenatable material is also preferably supplied to the first hydrogenation zone at a rate corresponding to a liquid hourly space velocity of from about 0.05 to about 5.0 h$^{-1}$.

If desired, the pressure and/or the temperature and/or the hydrogen-containing gas:condensable material(s) volume ratio can be adjusted in any convenient manner between the first and second hydrogenation zones and/or between the second and third hydrogenation zones. For example, the temperature can be adjusted by use of a heat exchanger or exchangers or by injection of relatively hotter or cooler hydrogen-containing gas. The latter method will also result in a corresponding change in the hydrogen-containing gas:condensable material(s) volume ratio.

The hydrogen-containing gas used in the process of the invention can be obtained in conventional manner. Preferably it contains at least about 50 volume % up to about 99.9 volume % or more, e.g. from about 80 to about 99 volume %, of hydrogen. It may further contain one or more inert gases, such as nitrogen or methane. Conveniently the hydrogen-containing gas is produced by pressure swing absorption.

The activity and selectivities of the three catalysts specifically mentioned above are under typical operating conditions as set out in Table 1 hereunder.

TABLE 1

| Catalyst | Selectivities (molar %) | | | Relative Activity |
|---|---|---|---|---|
| | THF | n-butanol | Acetal | |
| PG85/1 | 2–5 | 0.5 | 0.4 | 9 |
| DRD92/89A | 1–3 | 0.7 | 0.15 | 15 |
| DRD92/89B | 20–30 | 0.3 | 1.0–2.0 | 12 |

Notes:
1. "THF" means tetrahydrofuran.
2. "Acetal" means the cyclic acetal, 2-(4'-hydroxybutoxy)-tetrahydrofuran, of the formula:

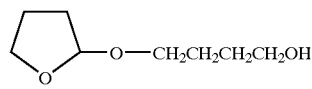

If desired bypass lines can be provided so that, when the hydrogenatable material has a sufficiently low content of acidic material, some or all of the vaporous stream normally supplied to the first hydrogenation zone can be fed directly to the second hydrogenation zone and/or so that some or all of the first intermediate product stream can be fed directly to the third hydrogenation zone and/or so that some or all of the second intermediate product stream can bypass the third hydrogenation zone. In this way the operator of a plant utilising the process of the invention can vary the amount of tetrahydrofuran or other $C_4$ to $C_{12}$ cyclic ether to take account of demand therefor.

Figure 2:
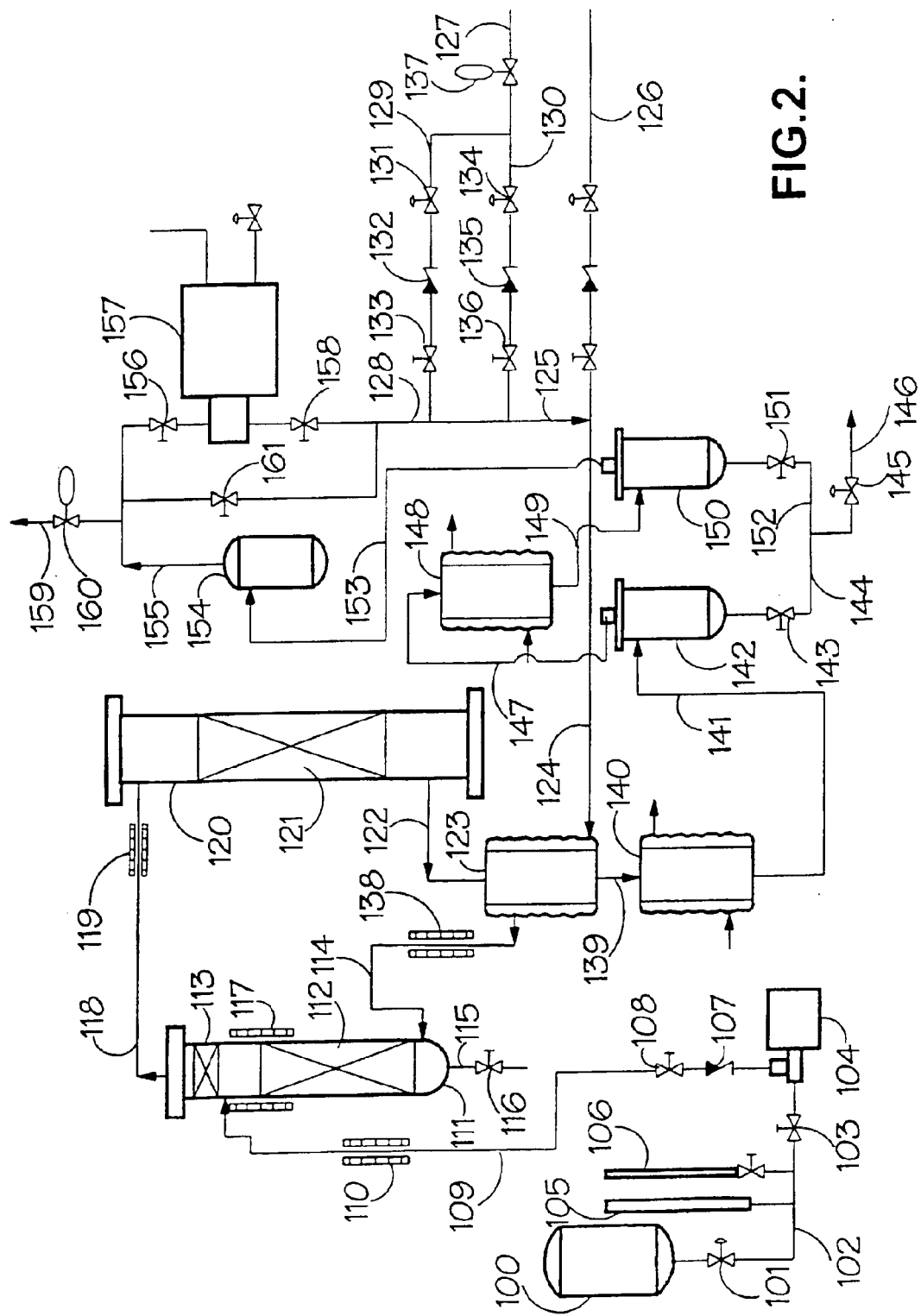

In order that the invention may be clearly understood and readily carried into effect, a preferred process in accordance therewith will now be described, by way of example only, with reference to the accompanying diagrammatic drawings, wherein:

FIG. 1 is a flow diagram of a plant for the co-production of butane-1,4-diol, tetrahydrofuran and γ-butyrolactone by hydrogenation of dimethyl maleate; and FIG. 2 is a flow diagram of an experimental apparatus for carrying out, on a laboratory scale, hydrogenation of diethyl or dimethyl maleate.

It will be understood by those skilled in the art that the drawings are diagrammatic and that further items of equipment such as reflux drums, pumps, vacuum pumps, compressors, gas recycle compressors, temperature sensors, pressure sensors, pressure relief valves, control valves, flow controllers, level controllers, holding tanks, storage tanks, and the like may be required in a commercial plant. The provision of such ancillary items of equipment forms no part of the present invention and is in accordance with conventional chemical engineering practice.

Referring to FIG. 1 of the drawings, there is illustrated a plant for the production of butane-1,4-diol and, as co-products, tetrahydrofuran and γ-butyrclactone by hydrogenation of dimethyl maleate in the vapour phase. In this plant dimethyl maleate is supplied from an esterification plant 1 of the type described in WO-A-90/08127. This comprises a number of esterification trays mounted one above the other, each containing a charge of a solid esterification catalyst, such as Amberlyst™ 16 resin, and each having a vapour upcomer for upflowing vapour and a liquid downcomer to permit liquid to flow down the column from one esterification tray to the next lower one. Methanol vapour is supplied to the bottom of column reactor while water of esterification is removed in the vapour stream exiting the top of the column reactor. Typical reaction conditions in the column reactor include use of a temperature of from about 110° C. to about 125° C. and a pressure of from about 1 bar to about 3 bar, while the residence time in the column reactor is usually about 3 hours. Normally the temperature on the top tray will be somewhat higher (e.g. about 125° C.) than that on the lowermost tray (e.g. about 115° C.)

The resulting dimethyl maleate in line 2 typically contains no more than about 2.0 wt/wt % of acidic organic materials, such as monomethyl maleate, and preferably less than about 0.5 wt/wt %, e.g. about 0.1 to about 0.35 wt/wt %, of acidic materials. It is pumped to near the top of a vaporiser column (not shown) which is operated at a temperature of 170° C. and a pressure of 885 psia (61.02 bar). The dimethyl maleate flows down the vaporiser column against an upflowing stream of hydrogen from line 3. A near saturated vapour mixture stream comprising dimethyl maleate in hydrogen, with a hydrogen:dimethyl maleate molar ratio of about 320:1 and at a temperature of from about 180° C. to about 195° C. and at a pressure of 900 psia (6102 kPa) is recovered from the top of the vaporiser column. It is diluted with further hot hydrogen at a temperature of from about 180° C. to about 195° C. to yield a vaporous stream with a hydrogen:dimethyl maleate molar ratio of about 350:1 and is at least about 5° C. above its dew point. It flows on in line 6 to hydrogenation unit 7. This includes three hydrogenation reactors 8, 9 and 10 connected in series and each containing a charge of a granular ester hydrogenation catalyst.

The vaporous mixture in line 6 flows on in line 11 to first hydrogenation reactor 8 which contains a charge 12 of PG85/1 copper chromite catalyst, in reduced form, and is operated at a temperature of about 173° C., an inlet pressure of 885 psia (6102 kPa), and an exit temperature of 190° C. (PG85/1 catalyst is available from Kvaerner Process Technology Limited of The Technology Centre, Princeton Drive, Thornaby, Stockton-on-Tees, TS17 6PY, England). The dimethyl maleate feed rate corresponds to a liquid hourly space velocity of 0.5 $h^{-1}$. Partial conversion of dimethyl maleate to butane-1,4-diol, tetrahydrofuran and γ-butyrolactone, as well as small quantities of undesirable byproducts, such as the cyclic acetal 2-(4'-hydroxybutoxy)-tetrahydrofuran, occurs in passage through reactor 8. In addition, hydrogenation of unreacted dimethyl maleate to dimethyl succinate occurs. The resulting first intermediate reaction mixture, which now has a low content of tetrahydrofuran, passes through lines 13, 14, 15, and 16 into second hydrogenation reactor 9 which contains a charge 17 of the manganese promoted copper hydrogenation catalyst DRD92/89B which is also available from Kvaerner Process Technology Limited. If desired, further hydrogen at an appropriate temperature either to heat the first intermediate product stream or to cool it, can be added from line 18 prior to entry to second hydrogenation reactor 9. Further hydrogenation occurs in passage through second hydrogenation reactor 9 and a second intermediate reaction product stream is recovered in line 19. Reactor 9 effectively acts as the tetrahydrofuran production zone of the plant so that this second intermediate reaction product stream contains, in addition to unreacted dimethyl succinate (and any remaining traces of unreacted dimethyl maleate), a much higher content of tetrahydrofuran than the first intermediate reaction product stream in line 13 and an acceptably low content of n-butanol. However, its content of the cyclic acetal, i.e. 2-(4'-hydroxybutoxy)-tetrahydrofuran, is generally unacceptably high.

This second intermediate reaction product stream is then passed on through lines 20, 21, and 22 to third hydrogenation reactor 10. Additional hydrogen at an appropriate temperature can, if desired, be added from line 23 to the second intermediate reaction product mixture in line 21 in order to adjust the temperature of the resulting stream prior to entry to third hydrogenation reactor 10. This third hydrogenation reactor 10 contains a charge 24 of the manganese promoted copper hydrogenation catalyst DRD92/89A which is also available from Kvaerner Process Technology Limited. This catalyst is highly active for the conversion of the remaining dimethyl succinate but exhibits the surprising result that the content of the cyclic acetal, i.e. 2-(4'-hydroxybutoxy)-tetrahydrofuran, in the final product stream in line 25 is much reduced compared with the content of this compound in the second intermediate reaction product stream in line 19.

The final reaction product mixture is recovered via lines 25 and 26 and is passed to a purification section 27 in which the crude hydrogenation product mixture is distilled in several stages to yield pure butane-1,4-diol in line 28. Lines for separate recovery of tetrahydrofuran and γ-butyrolactone are indicated at 29 and 30 respectively. n-butanol and other by-products are recovered as indicated by line 31 while unreacted hydrogen is recycled via lines 32 and 33 to form the recycle stream in line 5.

Line 34 allows reactor 8 to be bypassed wholly or in part while line 35 permits reactor 9 to be bypassed in a similar fashion. Lines 36 and 37 provide an alternative means for bypassing these reactors. By use of these bypass lines and suitable control valves (not shown), the three hydrogenation reactors 8, 9 and 10 can be connected at will in series or in parallel or can be used individually.

The invention is illustrated further in the following Examples.

EXAMPLE 1

The hydrogenation of diethyl maleate using a catalyst suitable for use in the first hydrogenation zone of the process of the invention was investigated using the experimental apparatus of FIG. 2.

Diethyl maleate which contained 0.05 wt/wt % of monoethyl maleate was fed from reservoir 100 by way of valve 101, line 102 and valve 103 to liquid feed pump 104. Burette 105 provided a buffer supply whilst burette 106 was fitted with a liquid level controller (not shown) that controlled valve 101 so as to ensure that liquid feed was supplied from reservoir 100 to liquid feed pump 104 at a constant head. The liquid feed was pumped through non-return valve 107 and isolation valve 108 into line 109, which could be heated by electrical heating tape 110, before the heated liquid entered the upper part of an insulated vaporiser vessel 111 above a bed of 6 mm×6 mm glass rings 112. A stainless steel demister pad 113 was fitted at the top end of the vaporiser vessel 111. A stream of hot hydrogen-containing gas was supplied to the bottom of vaporiser 111 in line 114. A liquid drain line 115 fitted with a drain valve 116 enabled withdrawal of any unvaporised liquid feed material (e.g. "heavies") from the base of the vaporiser vessel 111. A saturated vaporous mixture comprising diethyl maleate and hydrogen was recovered in line 118 from the top of vaporiser vessel 111. The vaporous mixture was heated by heating tape 119 in order to raise its temperature above the dew point of the mixture prior to entering the top end of hydrogenation reactor 120 which contained a bed of 121 of 250 ml of PG85/1 catalyst which is commercially available from Kvaerner Process Technology Limited. The compositions of this catalyst and of those used in Examples 2 to 7 are set out below in Table 2.

TABLE 2

| Catalyst | Composition (wt %) | | | | Acidity mmol/g | Surface area m²/g | Density g/cm³ | Pore volume mm³/g (%) | | | Surface area distribution m²/g (%) | | |
|---|---|---|---|---|---|---|---|---|---|---|---|---|---|
| | Cu | Cr | Mn | Al | | | | Super-macro | Macro | Meso | Super-macro | Macro | Meso |
| PG85/1 | 42.4 | 31.7 | — | — | 0.10 | 27 | 1.26 | 145.7 (58.37) | 100.2 (40.14) | 3.7 (1.48) | 3.861 (11.99) | 13.495 (41.89) | 14.856 (46.12) |
| DRD92/89A | 41.1 | — | 6.2 | 20.4 | 0.11 | 47 | 1.452 | 3.6 (1.72) | 186 (89.04) | 19.3 (9.24) | 0.131 (0.28) | 38.24 (81.41) | 8.6 (18.31) |
| DRD92/89B | 42.3 | — | 6.8 | 19.7 | 0.11 | 50 | 1.452 | 17.0 (8.57) | 115.7 (58.35) | 65.6 (33.08) | 0.70 (1.4) | 14.96 (29.92) | 34.34 (68.68) |

Notes:
1. "Super-macro" means pore sizes greater than 40 nm.
2. "Macro" means pore sizes in the range from 7 nm to 40 nm.
3. "Meso" means pore sizes less than 7 nm.

The vaporous mixture passed downward through catalyst bed 121. Conversion of diethyl maleate to a mixture of butane-1,4-diol, γ-butyrolactone, and tetrahydrofuran, as well as minor amounts of by-products, including the cyclic acetal 2-(4'-hydroxybutoxy)-tetrahydrofuran, occurred under adiabatic conditions as the vaporous mixture passed through the catalyst bed 121. Adiabaticity was maintained by electrical heating tapes (not shown) wrapped around reactor 120 under the control of appropriately positioned thermocouples (not shown) and by thermal insulation of the reactor 120. The overall reaction was exothermic with a general increase in catalyst bed temperature from the inlet end of catalyst bed 121 to its exit end. The hydrogenation product mixture exited the hydrogenation reactor 120 in line 122 and was passed through heat exchanger 123 which simultaneously cooled the hydrogenation product mixture and heated a supply of hydrogen-containing gas from line 124. Condensation of the bulk of the condensable products in line 122 occurred in heat exchanger 123. The gas in line 124 comprised hydrogen-containing gas from line 125 and, optionally, an inert gas or a mixture of inert gases such as nitrogen, argon, or methane supplied in line 126. The gas in line 125 comprised make-up hydrogen supplied in line 127 and recycle hydrogen supplied in line 128. Make-up hydrogen in line 127 could be supplied to line 125 in either or both of two streams in lines 129 and 130 via a system of pressure controllers 131 to 136 and a mass flow controller 137 from high purity hydrogen cylinders (not shown).

The heated hydrogen-containing gas from heat exchanger 123 passed on in line 114 and was heated further by electrical heating tape 138 for supply to the vaporiser vessel 111.

The cooled hydrogenation product from heat exchanger 123 passed on through line 139 to be cooled further in cooler 140 to a temperature near ambient temperature. The liquid/vapour mixture from cooler 140 passed on in line 141 to a first knockout pot 142 where liquid hydrogenation product was collected for eventual supply by means of valve 143, line 144, and control valve 145 to product line 146. A vaporous mixture comprising hydrogen and uncondensed ethanol exited the top of knockout pot 142 in line 147 and was further cooled to a temperature of 10° C. in cooler 148. The further cooled liquid/vapour mixture from cooler 148 was supplied via line 149 to a second knockout pot 150 wherein condensed methanol was collected for eventual supply through valve 151 and line 152 to product line 146. The gas and uncondensed materials from knockout pot 150 were supplied via line 153 through suction pot 154 into line 155 and then through valve 156 to gas recycle compressor 157. Gas was recycled through valve 158, lines 128, 125, 124 and 114 to vaporiser 111. In order to control the concentration of inert gases, such as nitrogen, in the circulating gas a purge gas stream could be bled from the system in line 159 under the control of valve 160.

Reference 161 represents a bypass valve.

At start up of the apparatus the charge of catalyst of bed 121 was placed in reactor 120 which was then purged with nitrogen. The catalyst bed 121 was then reduced carefully by a method similar to that described in EP-A-0301853.

Diethyl maleate was then pumped from reservoir 100 to the vaporiser 111 at a rate of 126 ml/h corresponding to a liquid hourly space velocity (LHSV) of 0.42 h$^{-1}$. The hydrogen-containing gas:diethyl maleate molar ratio in the vaporous mixture in line 118 was 520:1. The reactor 120 was maintained at an exit temperature of 180° C. and a pressure of 900 psia (62.05 bar). The hydrogenation zone was therefore operated under conditions which prevented the condensation of diethyl maleate, butane-1,4-diol, and γ-butyrolactone. The temperature throughout the reactor 120 was above the dew point at the operating pressure.

The liquid in line 146 was analysed periodically by capillary gas chromatography using a 25 m long, 0.32 mm internal diameter fused silica column coated internally with a 0.25 µm film of DB 1701, a helium flow rate of 2 ml/minute with a gas feed split ratio of 100:1 and a flame ionisation detector. The instrument was fitted with a chart recorder having a peak integrator and was calibrated using authentic samples of the products.

The results are set out below in Table 3.

EXAMPLE 2

The general procedure of Example 1 was followed but using a catalyst suitable for use in the second hydrogenation zone of the process of the invention. Thus the PG 85/1 catalyst of Example 1 was replaced by 250 ml of DRD 92/89 B catalyst available from Kvaerner Process Technology Limited. The results are included in Table 3 below.

EXAMPLE 3

The apparatus of Example 1 and the same general procedure was used except that the catalyst used was a catalyst suitable for use in the third hydrogenation zone of the process of the invention, i.e. 250 ml of DRD 92/89 A catalyst available from Kvaerner Process Technology Limited. The results are also included in Table 3 below.

TABLE 3

| Example No. | 1 | 2 | 3 |
|---|---|---|---|
| Inlet temperature ° C. | 169 | 173 | 174 |
| Exit temperature ° C. | 180 | 180 | 181 |
| Pressure psig (kPa absolute) | 887 (6217) | 885 (6203) | 855 (6203) |
| H$_2$:ester molar ratio | 532 | 522 | 450 |
| LHSV h$^{-1}$ | 0.50 | 0.42 | 0.42 |
| Selectivity mole % | | | |
| Tetrahydrofuran | 6.92 | 25.65 | 6.45 |
| n-butanol | 0.34 | 0.18 | 0.84 |
| γ-butyrolactone | 9.30 | 7.53 | 9.18 |
| Butane-1,4-diol | 83.45 | 66.64 | 83.17 |
| Unknowns | 1.26 | 0.25 | 0.33 |
| Diethyl succinate conversion mole % | 98.34 | 98.22 | 99.4 |
| "Peak acetal" weight % | 0.28 | 0.40 | 0.19 |

Notes:
1. The term "byproduct acetal" refers to the cyclic acetal, i.e. 2-(4'-hydroxybutoxy)-tetrahydrofuran of the formula:

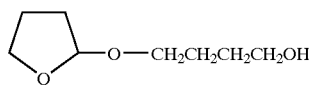

2. The "peak acetal" analysis was conducted by taking a sample of the crude product, evaporating tetrahydrofuran and ethanol therefrom, and heating for 2 hours at 160° C. under nitrogen, during the course of which samples were periodically quantitatively analysed by gas chromatography for the presence of the cyclic acetal. The highest reading obtained during this procedure was taken as the peak acetal value.

EXAMPLE 4

The apparatus of FIG. 2 was charged with three superposed beds of catalyst totalling 300 ml of catalyst in all. The catalyst of the top bed was the same as that used in Example 1, i.e. PG 85/1, while the catalyst of the middle bed was the same as that used in Example 2, i.e. DRD92/89B, and the catalyst of the bottommost bed was the same as that used in Example 3, i.e. DRD92/89A. The volume ratio of the three beds (top:middle:bottommost) was 25:37.5:37.5. The ester feedstock was the same diethyl maleate feedstock as used in Example 1. The same general procedure was used as in Example 1 and the results obtained are listed below in Table 4.

EXAMPLE 5

The same apparatus as used in Example 4 was supplied with dimethyl maleate containing about 0.5 wt/wt % of monomethyl maleate, using the same general procedure as in Example 1 with the results as given in Table 4 below.

EXAMPLE 6

The same general procedure as used in Example 4 was used with the exception that the volume ratio of the three catalyst beds (top:middle:bottommost) was 25:20:55. The same catalysts were used as in Example 4 and the same grade of diethyl maleate was used as feedstock. The results are included in Table 4 below.

EXAMPLE 7

The apparatus used in Example 6 was supplied with the same grade of dimethyl maleate as was used in Example 5. The results are as set out below in Table 4.

TABLE 4

| Example No. | 4 | 5 | 6 | 7 |
|---|---|---|---|---|
| Inlet temperature °C. | 159 | 160 | 169 | 174 |
| Exit temperature °C. | 179 | 189 | 180 | 190 |
| Pressure psig (kPa absolute) | 886 | 885 | 885 | 885 |
|  | (6210) | (6203) | (6203) | (6203) |
| $H_2$:ester molar ratio | 524 | 335 | 522 | 347 |
| LHSV $h^{-1}$ | 0.42 | 0.35 | 0.42 | 0.34 |
| Selectivity mole % |  |  |  |  |
| Tetrahydrofuran | 12.23 | 14.22 | 14.28 | 26.56 |
| n-butanol | 0.28 | 0.60 | 0.47 | 0.80 |
| γ-butyrolactone | 8.43 | 10.44 | 8.19 | 9.66 |
| Butane-1,4-diol | 79.07 | 74.74 | 77.07 | 62.99 |
| Unknowns | 0.20 | 0.49 | 0.21 | 0.64 |
| Dimethyl succinate conversion mole % | 98.4 | 99.25 | 99.4 | 99.64 |
| "Peak acetal" weight % | 0.23 | 0.26 | 0.17 | 0.23 |

EXAMPLES 8 AND 9

The apparatus of FIG. 2 was charged with fresh samples of catalyst in the same proportions as Example 4. It was supplied with a dimethyl maleate feed. The analysis of the catalysts used was as set out in Table 5. The results obtained were as set out below in Table 6.

TABLE 5

| Catalyst | Composition (wt %) | | | | Acidity | Surface | Density | Pore volume $mm^3/g$ (%) | | | Surface area distribution $m^2/g$ (%) | | |
|---|---|---|---|---|---|---|---|---|---|---|---|---|---|
|  | Cu | Cr | Mn | Al | mmol/g | area $m^2/g$ | $g/cm^3$ | Super-macro | Macro | Meso | Super-macro | Macro | Meso |
| PG85/1 | 42.8 | 31.4 | — | — | 0.10 | 27 | 1.306 | 118.58 | 107.5 | 8.0 | 3.232 | 11.275 | 2.900 |
|  |  |  |  |  |  |  |  | (50.67) | (45.92) | (3.41) | (18.57) | (64.79) | (16.64) |
| DRD92/89A | 45 | — | 6.4 | 18.3 | 0.11 | 47 | 1.438 | 3.5 | 134.8 | 30.3 | 0.112 | 27.715 | 13.497 |
|  |  |  |  |  |  |  |  | (2.08) | (79.95) | (17.97) | (0.27) | (67.07) | (32.66) |
| DRD92/89B | 43.8 | — | 7.3 | 18.2 | 0.10 | 42 | 1.590 | 2.6 | 104.4 | 40.7 | 0.116 | 13.497 | 21.306 |
|  |  |  |  |  |  |  |  | (1.76) | (70.68) | (27.56) | (0.333) | (38.652) | (61.015) |

Notes:
1. "Super-macro" means pore sizes greater than 40 nm.
2. "Macro" means pore sizes in the range from 7 nm to 40 nm.
3. "Meso" means pore sizes less than 7 nm.

TABLE 6

| Example No. | 8 | 9 |
|---|---|---|
| Inlet temperature °C. | 171 | 163 |
| Exit temperature °C. | 191 | 191 |
| Pressure psig (kPa absolute) | 885 | 609 |
|  | (6203) | (4299) |
| $H_2$:ester molar ratio | 350 | 246 |
| LHSV $h^{-1}$ | 0.34 | 0.34 |
| Selectivity mole % |  |  |
| Tetrahydrofuran | 27.97 | 20.03 |
| n-butanol | 0.76 | 0.73 |
| γ-butyrolactone | 9.44 | 19.65 |
| Butane-1,4-diol | 61.83 | 59.58 |
| Unknowns | 1.05 | 1.11 |
| Dimethyl succinate conversion mole % | 98.8 | 98.62 |
| "Peak acetal" weight % | 0.22 | 0.25 |

What is claimed is:

1. A process for the co-production of butane-1,4-diol and tetrahydrofuran by hydrogenation of a corresponding hydrogenatable material selected from mono-($C_1$ to $C_4$ alkyl) esters of dicarboxylic acids, di-($C_1$ to $C_4$ alkyl) esters of $C_4$ aliphatic dicarboxylic acids, γ-butyrolactone, and mixtures of two or more thereof, which comprises:

providing a plurality of hydrogenation zones including first, second and third hydrogenation zones connected in series, the hydrogenation zones each containing a charge of a granular ester hydrogenation catalyst, the first hydrogenation zone containing a bed of a catalyst which is tolerant of the presence of a minor amount of acidic material, the second hydrogenation zone containing a bed of a catalyst which provides enhanced selectivity to tetrahydrofuran compared to the catalyst of the first hydrogenation zone, and the third hydrogenation zone containing a bed of a catalyst which exhibits a reduced selectivity to at least one byproduct including 2-(4'-hydroxybutoxy)-tetrahydrofuran compared with the catalyst of the second hydrogenation zone;

maintaining each of the plurality of hydrogenation zones under temperature and pressure conditions effective for the hydrogenation of the hydrogenatable material to butane-1,4-diol;

supplying to the first hydrogenation zone at a feed temperature of from about 100° C. to about 300° C. and at a feed pressure of from about 50 psia (344.74 kPa) to 2000 psia (13789.52 kPa) a vaporous stream comprising hydrogen and the hydrogenatable material, the hydrogenatable material containing from 0.01% to 10% by weight of acidic material and being supplied at a rate corresponding to a liquid hourly space velocity of from 0.05 $hr^{-1}$ to 5.0 $hr^{-1}$;

recovering from the first hydrogenation zone a first intermediate product stream containing unreacted hydrogenatable material, butane-1,4-diol, γ-butyrolactone, tetrahydrofuran and one or more byproducts including 2-(4'-hydroxybutoxy)-tetrahydrofuran;

supplying material of the first intermediate product stream to the second hydrogenation zone;

recovering from the second hydrogenation zone a second intermediate product stream comprising unreacted hydrogenatable material, butane-1,4-diol, γ-butyrolactone, tetrahydrofuran and one or more byproducts including 2-(4'-hydroxybutoxy)-tetrahydrofuran, the selectivity to tetrahydrofuran being higher in the second intermediate product stream than in the first intermediate product stream;

supplying material of the second intermediate product stream to the third hydrogenation zone; and recovering from the third hydrogenation zone a final product stream which is substantially free of the hydrogenatable material and which contains butane-1,4-diol, γ-butyrolactone, tetrahydrofuran and byproducts including 2-(4'-hydroxybutoxy)-tetrahydrofuran, the selectivity to tetrahydrofuran being greater in the final product stream than in the first intermediate product stream and the selectivity to 2-(4'-hydroxybutoxy)-tetrahydrofuran being less in the final product stream than in the second intermediate stream.

2. A process according to claim 1, in which the hydrogenation catalyst of the first hydrogenation zone is selected from a noble metal hydrogenation catalyst and a copper-containing hydrogenation catalyst.

3. A process according to claim 2, in which the catalyst of the first hydrogenation zone is a copper-containing catalyst.

4. A process according to claim 2, in which the copper-containing catalyst is selected from reduced copper oxide/zinc oxide hydrogenation catalysts, reduced manganese promoted copper catalysts, reduced copper chromite catalysts, and reduced promoted copper chromite catalysts.

5. A process according to claim 2, in which the catalyst of the first hydrogenation zone is a palladium catalyst, a reduced copper chromite catalyst or a reduced promoted copper chromite catalyst.

6. A process according to claim 1, in which the catalyst of at least one of the second and third hydrogenation zones is a reduced manganese promoted copper catalyst.

7. A process according to claim 6, in which the second hydrogenation zone contains a bed of a reduced manganese promoted copper catalyst which has, in the unreduced form, a total surface area of at least about 15 m$^2$/g, a pore size distribution such that more than 50% of the pore volume is provided by pores in the size range less than about 40 nm, and a surface area distribution such that more than 50% of the total surface area is provided by pores of less than about 7 nm.

8. A process according to claim 6, in which the third hydrogenation zone contains a charge of a reduced manganese promoted copper catalyst which has, in the unreduced form, a total surface area of at least about 15 m$^2$/g, a pore size distribution such that more than 50% of the pore volume is provided by pores in the size range less than about 40 nm, and a surface area distribution such that more than 50% of the total surface area is provided by pores in the size range of from about 7 nm to about 40 nm.

9. A process according to claim 1, in which the charge of catalyst in the first hydrogenation zone is sufficiently large to reduce the content of acidic material in the first intermediate product stream to less than about 0.005% by weight.

10. A process according to claim 1, in which the hydrogenatable material is selected from monomethyl maleate, monomethyl fumarate, monomethyl succinate, dimethyl maleate, dimethyl fumarate, dimethyl succinate, γ-butyrolactone, and mixtures of two or more thereof.

11. A process according to claim 1, in which the hydrogenatable material is selected from monoethyl maleate, monoethyl fumarate, monoethyl succinate, diethyl maleate, diethyl fumarate, diethyl succinate, γ-butyrolactone, and mixtures of two or more thereof.

12. A process according to claim 1, in which the feed stream to each of the hydrogenation zones is a vaporous feed stream and in which the final product stream is recovered in vaporous form.

13. A process according to claim 1, in which the final product is recovered as a mixture of liquid and vapour at a temperature below the dew point of the stream.

14. A process according to claim 13, in which the feed stream to at least one hydrogenation zone downstream from the first hydrogenation zone is a mixture of vapour and liquid at a temperature below the dew point of the mixture.

15. A process according to claim 1, in which the hydrogen-containing gas:hydrogenatable material molar ratio in the vaporous feed mixture to the first hydrogenation zone is from about 50:1 to about 1000:1.

16. A process according to claim 1, in which the feed temperature to the first hydrogenation zone is from about 150° C. to about 250° C.

17. A process according to claim 1, in which the feed pressure to the first hydrogenation zone is from about 450 psia (about 3102.64 kPa) to about 1000 psia (about 6894.76 kPa).

* * * * *